United States Patent [19]
Yamazaki et al.

[11] Patent Number: 5,469,429
[45] Date of Patent: Nov. 21, 1995

[54] X-RAY CT APPARATUS HAVING FOCAL SPOT POSITION DETECTION MEANS FOR THE X-RAY TUBE AND FOCAL SPOT POSITION ADJUSTING MEANS

[75] Inventors: Masahiko Yamazaki; Yutaka Shibata; Kozi Natori; Mitsuru Yahata; Kyojiro Nambu, all of Tochigiken, Japan

[73] Assignee: Kabushiki Kaisha Toshiba, Kanagawa, Japan

[21] Appl. No.: 246,665

[22] Filed: May 20, 1994

[30] Foreign Application Priority Data

May 21, 1993 [JP] Japan .................... 5-119656

[51] Int. Cl.⁶ ...................................... A61B 6/00
[52] U.S. Cl. .................... 378/19; 378/113; 378/207
[58] Field of Search .................... 378/11, 12, 14, 378/15, 19, 20, 137, 138, 205, 207, 113, 193

[56] References Cited

U.S. PATENT DOCUMENTS

| | | | |
|---|---|---|---|
| 3,965,357 | 6/1976 | Hounsfield | 378/11 |
| 4,211,925 | 7/1980 | Fairbairn | 378/12 |
| 4,675,891 | 6/1987 | Plessis et al. | 378/207 X |
| 4,827,494 | 5/1989 | Koenigsberg | 378/138 |
| 4,991,189 | 2/1991 | Boomgaarden et al. | |
| 5,065,420 | 11/1991 | Levene | 378/137 |

FOREIGN PATENT DOCUMENTS 2-91200  7/1990  Japan .

*Primary Examiner*—David P. Porta
*Attorney, Agent, or Firm*—Finnegan, Henderson, Farabow, Garrett & Dunner

[57] ABSTRACT

An X-ray computerized tomographic (CT) apparatus capable of facilitating alignment of focal spot position at the time of replacing an X-ray tube anew and capable of easily correcting the focal spot position even when the focal spot position of the X-ray tube is deviated. Thereby, the focal spot position of the X-ray tube remains fixed in a predetermined position. The X-ray computerized tomographic (CT) apparatus includes an X-ray tube which is freely movable in at least one of a horizontal direction and a vertical direction; a detection unit for detecting a dislocated degree of the focal spot position of the X-ray tube; and a controlling unit for automatically controlling the focal spot position of the X-ray tube based on data obtained from the detection unit so that the focal spot position of the X-ray tube remains fixed in a predetermined position. In a case where the CT apparatus is used for a helical scanning operation, the detection unit may further include a detection timing controller for controlling an instance of detection and alignment of the focal spot position by utilizing only an output of the X-ray amount detected at a predetermined position of a gantry.

12 Claims, 7 Drawing Sheets

X-RAY CT APPARATUS HAVING FOCAL SPOT POSITION DETECTION MEANS FOR THE X-RAY TUBE AND FOCAL SPOT POSITION ADJUSTING MEANS

BACKGROUND OF THE INVENTION

1. Technical Field

The present invention relates to an X-ray optical system of a computerized tomographic (CT) apparatus. It particularly relates to the CT apparatus equipped with a mechanism which adjusts a focal point position of an X-ray tube.

2. Background Art

In general, when an X-ray tube for an X-ray computerized tomographic (CT) apparatus is replaced with a new tube, alignment in both lateral and longitudinal directions is needed in order to adjust a focal spot position of the X-ray tube. Referring to FIG. 1, an X-ray tube 101 is mounted to a plate 102 which is used for alignment in the lateral direction. The alignment plate 102 is attached to a plate 103 which is used for alignment in the longitudinal direction. In the plates 102, 103, there is provided respectively a guide rail 104 along which the alignment plates 102, 103 are moved so as to to align the focal spot position of the X-ray tube, by manually operating a fine-adjustment member 105.

Then, an amount to be finely adjusted in the lateral direction is obtained by an X-ray amount profile in a channel direction when a pin-phantom is scanned. The phantom is supported by a pin-shaped material and is positioned in a rotation center of the CT apparatus The finely adjusted amount in the longitudinal direction is obtained by a profile of the X-ray data in a slice thickness direction. Then, a tool having a slit therein, which is movable in the longitudinal direction is mounted to and in front of an X-ray detector.

As described above, after the alignment of the focal spot position in both lateral and longitudinal positions are made, the position of the X-ray tube is fixed.

However, in the event that the alignment of the X-ray tube focal spot position Is manually carried out, a service attendant for the alignment has to go through difficult and cumbersome task for positioning the focal spot.

Moreover, when the focal spot position is moved due to some reasons such as a thermal expansion of a target or anode in the X-ray tube, there occurs a ring like image artifact accompanied by the movement of the focal spot position. However, it is not easy to correct the focal spot position once the X-ray tube position is fixed, so that the image artifact caused thereby has been a troublesome factor.

Moreover, a slit that controls the X-ray amount is moved in the conventional practice, as described in a U.S. Pat. No. 4,991,189 granted to Boomgaarden et al. of General Electric Company on Feb. 5, 1991. As a result, a desired slice position and an X-ray path moved according to movement of the focal spot position can not coincide. Consequently, a spatial resolution and so on thus obtained are greatly deteriorated when a helical scanning operation is performed.

SUMMARY OF THE INVENTION

In view of the foregoing drawbacks, it is therefore an object of the present invention to provide an X-ray computerized tomographic (CT) apparatus capable of facilitating alignment of focal spot position at the time of replacing an X-ray tube anew and capable of easily correcting the focal spot position even when the focal spot position of the X-ray tube is deviated.

To achieve the object, there is provided an X-ray computerized tomographic (CT) apparatus having an X-ray detector, comprising: an X-ray tube which is freely movable in at least one of a horizontal direction and a vertical direction; detection means, disposed in the vicinity of the X-ray detector, for detecting a dislocated degree of the focal spot position of the X-ray tube; and means for automatically controlling the focal spot position of the X-ray tube based on data obtained from the detection means so that the focal spot position of the X-ray tube remains fixed in a predetermined position.

There is also provided an X-ray computerized tomographic (CT) apparatus for use with a helical scanning operation having an X-ray detector, the apparatus comprising: an X-ray tube which is freely movable in at least one of a horizontal direction and a vertical direction; detection means, provided in the vicinity of the X-ray detector for detecting a dislocated degree of the focal spot position of the X-ray tube; and means for automatically controlling the focal spot position of the X-ray tube based on data obtained from the detection means so that the focal spot position of the X-ray tube remains fixed in a predetermined position, wherein the detection means includes a detection timing means for controlling an instance of detection and aligning tile focal spot position by utilizing only an output of the X-ray amount detected at a predetermined position of a gantry.

One advantage of the present invention is that it provides to eliminate a ring-like image artifact accompanied with movement in the focal spot position.

Another advantage of the present invention is that the focal spot position of the X-ray tube can be kept constant without moving the X-ray tube, by deflecting the electron beam emanated from an electron gun.

BRIEF DESCRIPTION OF THE DRAWINGS

These and other objects, features and advantages of the present Invention will become more apparent from the following description of the preferred embodiment taken in conjunction with the accompanying drawings, in which.

DETAILED DESCRIPTION OF THE PREFERRED EMBODIMENTS

Features of the present invention will become apparent in the course of the following description of exemplary embodiments which are given for illustration of the invention and are not intended to be limiting thereof. Embodiments of the present invention will now be described with reference to the drawings.

EMBODIMENT NO. 1

Figure 1:
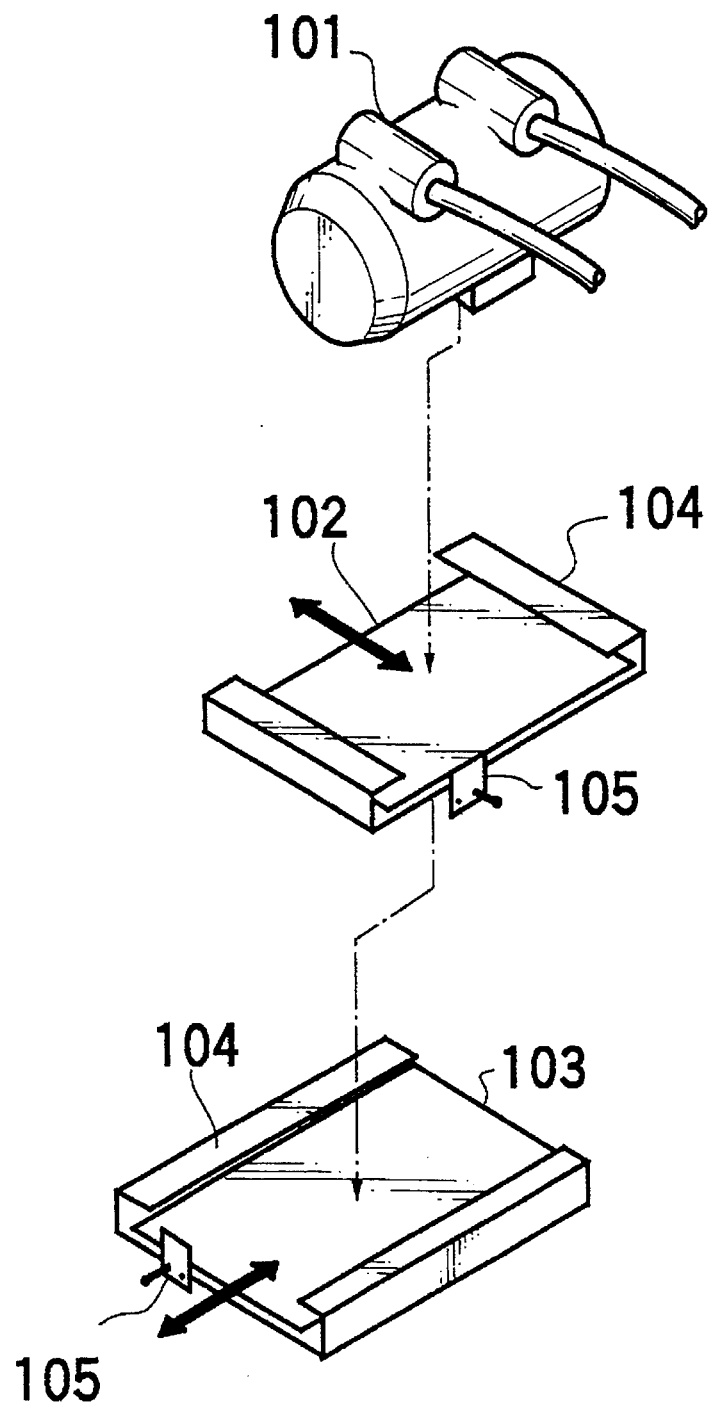
FIG. 1 is a perspective view showing how the alignment for the X-ray tube is carried out according to the conventional practice.
Figure 2:
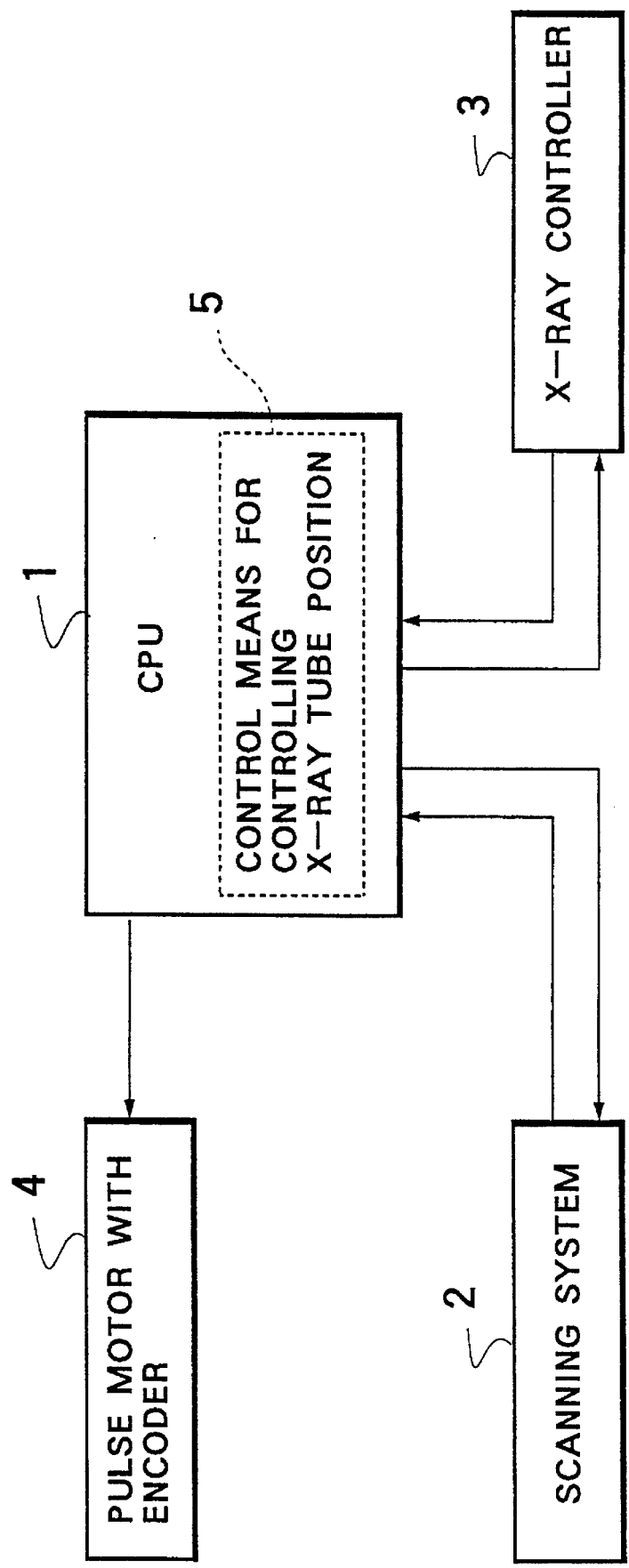
FIG. 2 is a block diagram of an X-ray computerized tomographic (CT) apparatus according to a first embodiment of the present invention.

FIG. 2 is a block diagram of an X-ray computerized tomographic (CT) apparatus according to a first embodiment of the present invention.

Figure 3:
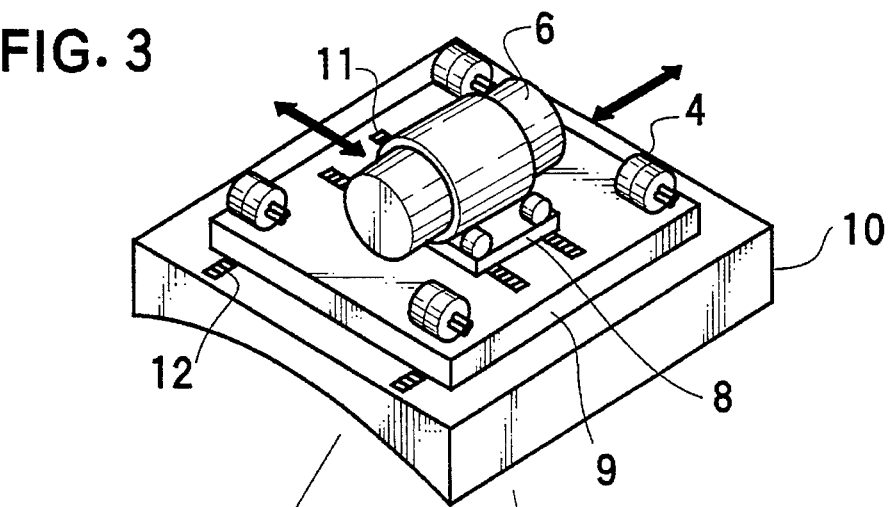
FIG. 3 is a perspective view showing a scanning system of the CT apparatus shown in FIG. 2.
Figure 3:
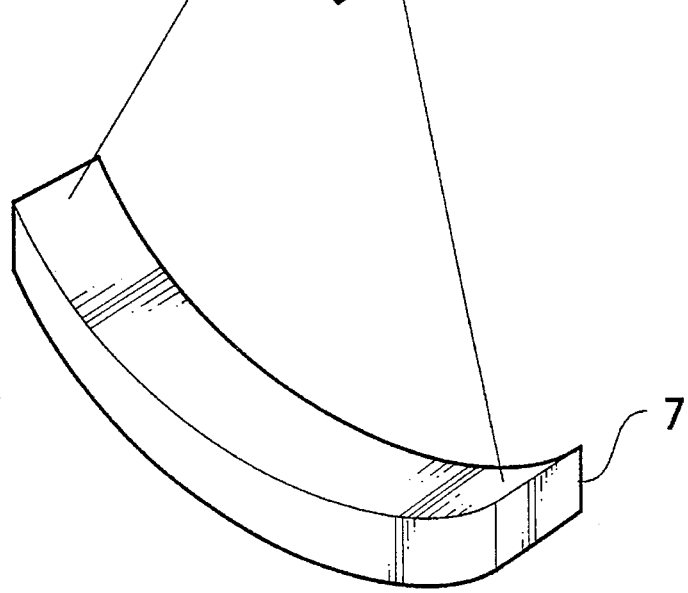

FIG. 3 is a perspective view showing a scanning system of the CT apparatus shown in FIG. 2.

Figure 4:
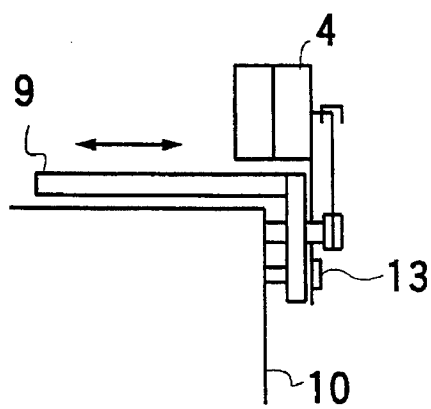
FIG. 4 shows a fine-adjustment member 13 of the CT apparatus shown in FIG. 2.

FIG. 4 shows a fine-adjustment member of the CT apparatus shown in FIG. 2.

Referring to FIG. 2, there is provided a central processing unit (CPU) 1 serving as a central control apparatus for a whole CT system. Under a control of the CPU 1, a scanning system 2, an X-ray controller 3, a pulse motor 4 with an encoder attached thereto (up to 10 μm precision) and the like are controlled. The CPU 1 is equipped with X-ray tube position controlling means 5 by which adjustment for the focal spot position of the X-ray tube 6 is controlled.

Referring to FIG. 3, in the scanning system 2, the X-ray tube 6 and an X-ray detector 7 are configured counter to each other so that a biological body to be examined is interposed between the tube 6 and the detector 7. The X-ray tube 6 generates an X-ray beam and the X-ray detector 7 detects the X-ray beam which emanates from the X-ray tube 6 and is transmitted through the biological body (not shown in FIG. 3).

Referring still to FIG. 3, the X-ray tube 6 is mounted to a horizontally movable tube alignment plate 8. The horizontally movable tube alignment plate 8 is mounted to the longitudinally movable tube alignment plate 9. The longitudinally movable tube alignment plate 9 is mounted to a fixed portion 10. The directions of the movable plates and 9 are perpendicular to each other.

On the horizontally movable tube alignment plate 9, there is provided a guide fall 11 for alignment use in the horizontal direction, so that the alignment plate 8 slidably mounted on the alignment plate 9 is slidable along the guide rail 11.

Similarly, on the fixed portion 10, there is provided a guide fall 12 for alignment use in the longitudinal direction, so that the alignment plate 9 slidably mounted on the fixed portion 10 is slidable along the guide rail 12. The horizontally movable tube alignment plate 8 and the longitudinally movable tube alignment plate 9 are controlled to be slidable in the horizontal and longitudinal directions, respectively, by means of a fine-adjustment member 13 (shown FIG. 4) which is driven by the pulse motor 4 with the encoder, so that the focal spot position of the X-ray tube 6 can be accurately adjusted.

Accordingly, when the X-ray tube 6 is replaced anew or when the alignment of the focal spot position of the X-ray tube 6 is performed, an instruction to acquire exposure data is given to tile scanning system 2 from the CPU 1 so as to acquire the exposure data. In accordance with the exposure data thus acquired, the fine-adjustment amount in the lateral (horizontal) and longitudinal directions is calculated. Then, an instruction signal is sent to the X-ray tube position controlling means 5 so that the horizontally movable tube alignment plate 8 and the longitudinally movable tube alignment plate 9 are moved by tile calculated fine-adjustment amount. Thereafter, in accordance with control of the X-ray tube position controlling means 5, the pulse motor with the encoder is driven. Thereby, the horizontally movable tube alignment plate 8 and the longitudinally movable tube alignment plate 9 are slid horizontally and longitudinally along -the guide rails 11 and 12, respectively, so as to automatically perform the the alignment of the focal spot position of the X-ray tube 6.

The fine-adjustment amount for the alignment plates 8, 9 are, for example, calculated and obtained in the following manner.

In order to obtain the fine-adjustment amount in the horizontal (lateral) direction, first the phantom is scanned, and data on a profile of the X-ray amount is acquired in a channel direction, where the channel direction indicates the circumferential direction along detector arrays.

Figure 5:
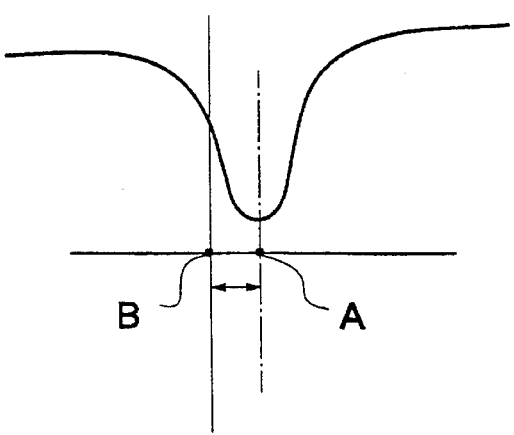
FIG. 5 is a profile of tile X-ray amount in the channel direction, when the pin phantom is scanned.

Referring to FIG. 5, there is shown an example of the profile of the X-ray amount where the horizontal axis indicates the channel direction and the vertical axis perpendicular to the horizontal axis indicates the X-ray amount detected (output). In the profile shown in FIG. 4, the fine-adjustment amount in terms of the horizontal (lateral) direction is obtained by taking difference between a central point B and a point A, in order that the point A and point B coincide. The point A is a point where the X-ray amount becomes minimum.

Figure 6:
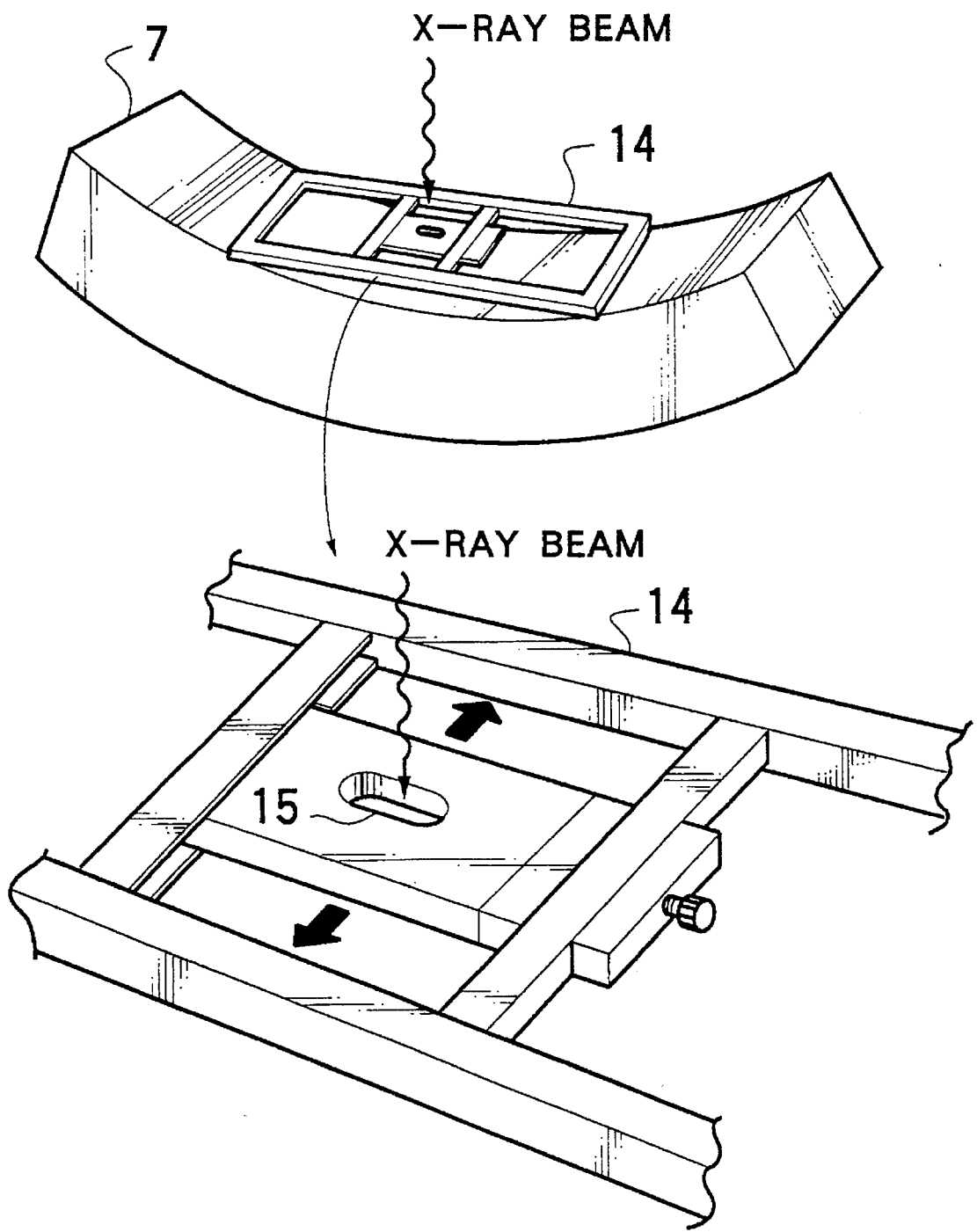
FIG. 6 is a perspective view showing the X-ray detector 7 on which the longitudinal (vertical) direction alignment tool 14 is mounted.

In order to obtain the fine-adjustment amount in the vertical (longitudinal) direction, first a longitudinal-direction alignment tool 14 as shown in FIG. 6 is mounted in front of the X-ray detector 7. The longitudinal-direction alignment tool 14 has a slidable slit 15 which is slidable in the longitudinal direction by means of a drive unit or manually. The slidable slit 15 is moved in the direction indicated by arrowmarks shown in FIG. 6 so that data on the profile of tile X-ray amount in the slice direction are acquired, wherein the X-ray amount means an amount of X-ray emanated from the X-ray tube 6 that passes through the slit to reach the detector unit 7. Similar to the above-mentioned procedure for aligning the focal spot position of the X-ray tube in the horizontal (lateral) direction, the fine-adjustment amount in terms of the vertical (longitudinal) direction is obtained by taking difference between a central point D and a point C, in order that tile point C and point D coincide. The point C is a point where the X-ray amount becomes minimum.

In a usual scanning mode, how much load is applied to the X-ray tube 6 is monitored based on OLP (over load protection) data which is sent from the X-ray controller 3 to the CPU 1. The OLP data are theoretical values by which there can be obtained information regarding how much a target is heated and how long the target need be cooled off. The OLP data are indicated in a unit of %, where 0% indicates no use of the target while the 100% indicates a point where the target melts out. Simultaneously, the data on fine-adjustment amount of the focal spot position for the X-ray tube 6 is transferred from the CPU 1 to the X-ray tube position controlling means 5. Thereafter, by driving the pulse motor 4 with the encoder in accordance with the control of the the X-ray tube position controlling means 5, the alignment of the focal spot position for the X-ray tube 6 may be performed between cycles of scanning operation such as a rapid sequence scanning. Here, in the rapid sequence scanning operation, every time a single rotation of the scanning is completed, a tabletop on which a patient lies is moved with a predetermined pitch in order to obtain another slice tomographic image.

It shall be appreciated that there may be utilized data such as a temperature of the target which is directly measured, instead of tile OLP data.

It shall be appreciated that the alignment of the focal spot position may be made during a rotation in the rapid sequence scanning operation.

As have been described, the alignment for the focal spot position of the X-ray tube 6 can be automatically performed without relying on a manual control at the time that the maintenance and inspection is carried out and the X-ray tube 6 is replaced anew. Therefore, a burden for the service attendant is significantly reduced. Moreover, even if the focal spot position is dislocated due to the thermal expansion of the target or the like in a usual scanning under clinical use or in a helical scanning operation (detail therefor will be described below), the focal spot position of the X-ray tube is optimally corrected, i.e., tile dislocated X-ray beam path is brought back to the original X-ray beam path smoothly. Thereby, the occurrence of the ring-like image artifact can be eliminated.

As mentioned above, there are used the data on the profile of the X-ray amount to calculate the fine-adjustment amount as illustrated in FIG. 5, at the time that the maintenance and inspection is carried out and the X-ray tube 6 is replaced anew. Besides, it shall be appreciated that both the data on the profile of the X-ray amount and the OLP information may be utilized to obtain the fine-adjustment amount. In this case, a state of the X-ray tube 6 is preferably obtained in conjunction with the OLP data (for example at 0%, 50%, 100%, respectively) in advance, so as perform the alignment of the focal spot position of the X-ray tube 6.

As described before, besides tile usage of the OLP data, the temperature of the X-ray tube 6 may be directly measured so as to obtain the fine-adjustment amount, in order to grasp the state of the X-ray tube 6.

WHEN AND HOW THE FOCAL SPOT SHALL BE ALIGNED USING HELICAL SCANNING SYSTEM

Next, described in detail is when and how the alignment of the focal spot position of the X-ray tube 6 is preferably performed in a helical scanning mode.

First, let us define a control response time t which is a time duration covering the following three basic instances:

(1) detection of dislocation of the focal spot position of the X-ray tube 6;

(2) start at which the focal spot position of the X-ray tube 6 is controlled; and (3) completion of the control of the focal spot position.

If a cycle of the control response time t equals to some few projections such as 1 msec, the alignment or correction operation may be made for every projection. Alternatively, the correction operation may be made by taking an average value for some predetermined number of projections. For example, when the correction is made for each projection, it will be made for every rotation degree of 5°–10°. When there are, for example, 1000 projections for one rotation of the gantry, average data among, for example 50 projections, may be taken, and for every 50 projections the correction is made based on the average value.

If the control response time t takes one rotation of the gantry or approximately 1 second or the like (in other words, the control response is rather slow), an average value of the focal spot position detecting unit corresponding to the one rotation of the gantry is used so that the correction operation is made for the next rotation. In this case, it is preferable to use only an output of the focal spot position obtained at predetermined position of the gantry. This is because the focal spot may be changed during a full cycle of rotation due to a slight distortion of the gantry itself.

As a result, tills slight amount of distortion is also attributed to the change of the focal spot position in addition to the thermal expansion of the anode. In order to avoid such an disadvantage mentioned above, it is preferable to take an average for the one rotation, or preferable that the position to measure the output of the focal spot position detecting unit be determined at a specific position, for example 90° degrees. Thereby, accuracy in adjusting the dislocation of the focal spot position due to the thermal expansion is further improved.

Regarding more specifically the slight distortion of the gantry, there occurs an apparent focal spot dislocation due to the fact that the gantry is slightly distorted. This slight distortion of the gantry is caused by the weight of parts mounted on a rotating portion of the gantry. Therefore, it is necessary to distinguish a pure factor responsible for the focal spot dislocation (caused by the thermal expansion or the like) from a different factor caused by the tile weights of of the parts in the gantry, otherwise the different factor may serve as erroneous factors. On the other hand, the dislocation of the focal spot has the nature of repeatability. Thus, the dislocation degree is constant at a same rotational position. Therefore, if the position to measure the output of the focal spot position detecting unit is determined at the specific position, for example, 90° degrees, the dislocated degree at the specific rotational position would be the same, so that tile dislocation degree can always be cancelled out.

Although an example of utilizing this technique was shown with the helical scanning mode, the above technique is also applicable to a dynamic scanning operation and other continuous scanning operations.

EXAMPLES OF HOW TO CALCULATE DISLOCATED AMOUNT OF THE FOCAL SPOT POSITION OF THE X-RAY TUBE 6

Figure 10:
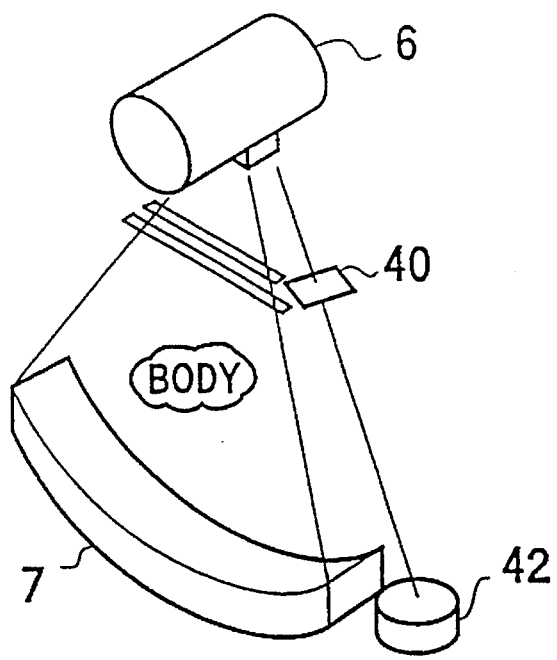
FIG. 10 shows a CT apparatus including a silt or a pinhole 40 for use with focal spot position detection, and a focal spot position detecting unit 42.
Figure 11:
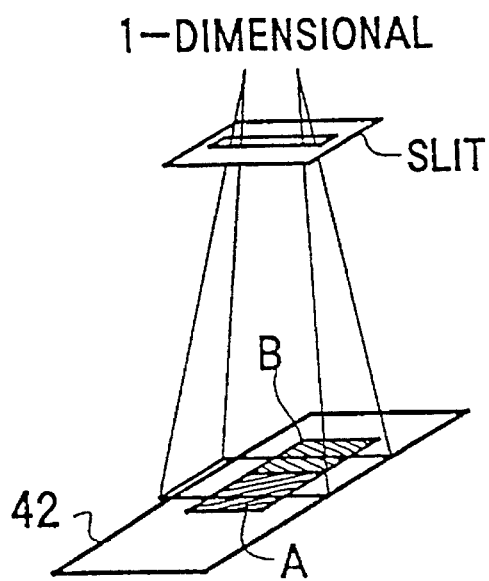
FIG. 11 illustrates the slit 40 and the focal spot position detecting unit 42 shown in FIG. 11, in order to detect a one-dimensional deviation of the focal spot position.

Referring to FIG. 10–FIG. 11, how to calculate the dislocated degree of the focal spot position of the X-ray tube 6 will be described.

There is provided a focal spot position detecting unit 42. In the vicinity of the X-ray tube 6, there is provided a slit 40 or pin hole 40 which is utilized with the focal spot position detecting unit 42. It is appreciated the position at which the focal spot position detecting unit 42 is provided is not limited to the position shown in FIG. 10. The X-ray detector 7 may serve as the focal spot position detecting unit itself.

Referring to FIG. 11 which illustrates how to detect the dislocation of the focal spot position of the X-ray tube 6 in the one-dimensional aspect (in the slice direction), the focal spot position detecting unit 42 is divided into two portions A and B. In order to detect the dislocation of tile focal spot position, the outputs of the X-ray amount detected at detectors A, B can be processed using the following function, for example, $$(A-B)/(A+B)$$

When this value is made a barometer of the focal spot position, the focal pot position can be monitored thereby.

STRUCTURE INSIDE THE X-RAY TUBE 6 AND VARIATIONS FOR KEEPING CONSTANT THE X-RAY BEAM PATH

Figure 12:
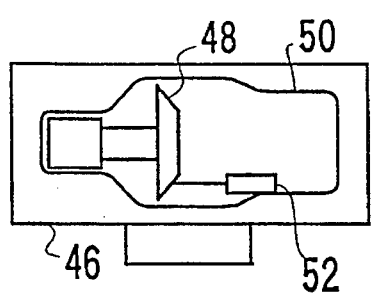
FIG. 12 shows an internal structure of the X-ray tube 6.

FIG. 12 shows an internal structure of the X-ray tube 6, which includes a housing 46 for enclosing a whole X-ray tube system; a target or anode 48, a filament 52 and an insert tube 50 that encloses the target 48 and the filament 52.

Various techniques for keeping constant the X-ray beam path are described below with reference to FIGS. 13A through 13D.

Figure 13A:
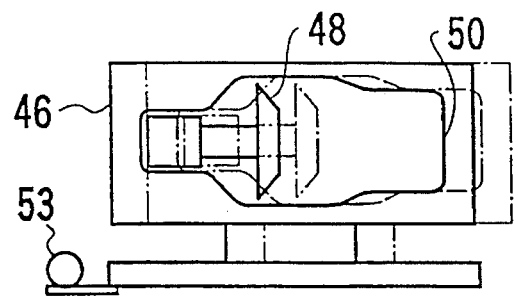
FIG. 13A illustrates a case where the X-ray beam path is kept constant by changing the position of a housing 46.

FIG. 13A illustrates a case where the X-ray beam path is kept constant by changing tile position of a housing 46. In the same figure, even when the position of the target 48 is dislocated due to the thermal expansion or the like, the housing 46 is moved by driving a motor 53 connected to the housing 46.

Figure 13B:
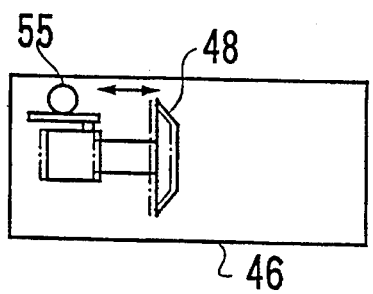
FIG. 13B illustrates a case where the X-ray beam path is kept constant by changing the position of a target 48.

FIG. 13B illustrates a case where the X-ray beam path is kept constant by changing the position of a target 48. In the same figure, even if the position of the target 48 is dislocated due to tile thermal expansion or the like, the target 48 itself is moved by the dislocated amount, so that tile X-ray beam path is kept constant. The target 48 may be driven by a motor 55 connected to the target 48.

Figure 13C:
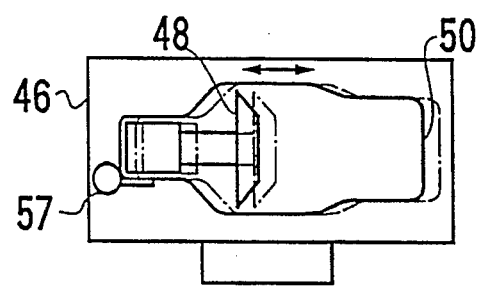
FIG. 13C illustrates a case where the X-ray beam path is kept constant by changing the position of an insert tube 50.

FIG. 13C illustrates a case where the X-ray beam path is kept constant by changing the position of an insert tube 50. Similar to tile case shown in FIG, 13A, even if the position of tile target 48 is dislocated due to the thermal expansion or tile like, the insert tube 50 is moved by driving a motor 57 connected to the insert tube.

Figure 13D:
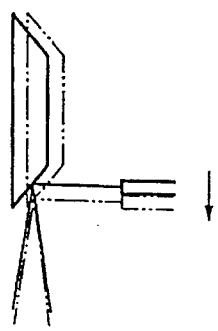
FIG. 13D illustrates a case where the X-ray beam path is kept constant by changing the position of a filament 52.
Figure 14:
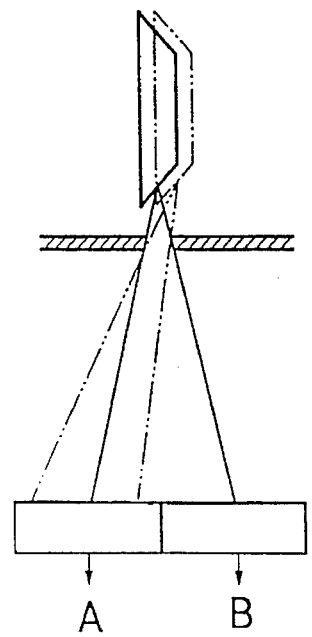
FIG. 14 illustrates how to detect the change of the focal spot position (in the one-dimensional case), according to the present invention, especially for the second embodiment.

FIG. 13D illustrates a case where the X-ray beam path is kept constant by changing the position of a filament 52. In the same figure, even if the position of the target 48 is dislocated due to the thermal expansion or the like, the filament 52 is moved so that the X-ray beam can be kept at a constant path.

EMBODIMENT NO. 2

Figure 7:
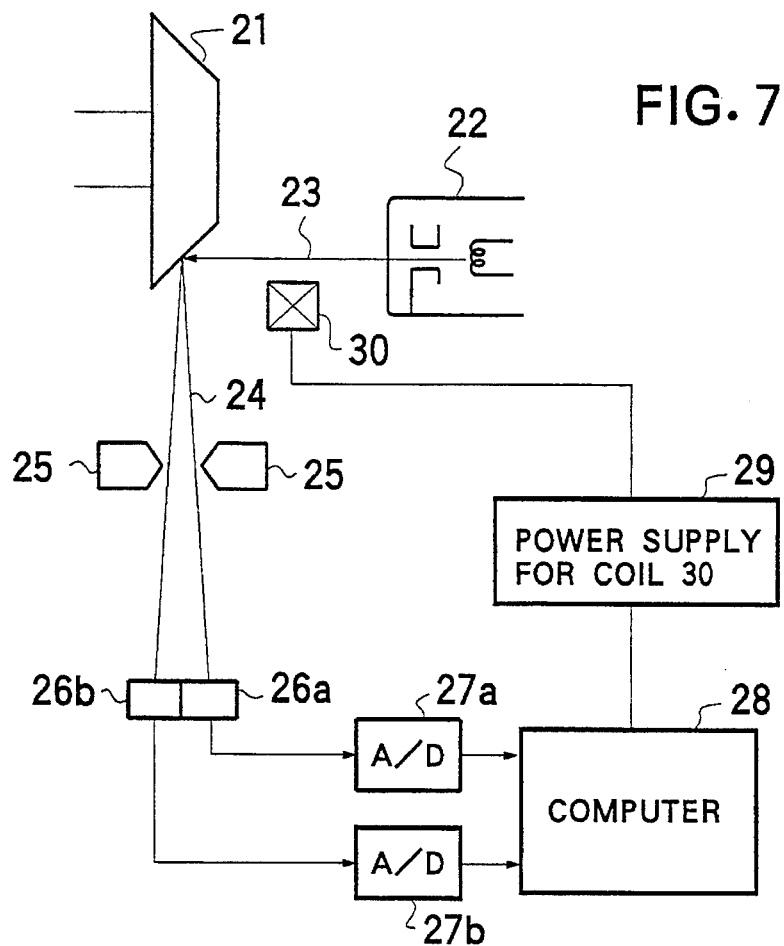
FIG. 7 illustrates a CT apparatus according to the second embodiment of the present invention.

FIG. 7 shows a CT apparatus having means for detecting the dislocation of the focal spot position of the X-ray tube and means for adjusting the deviated X-ray beam path, according to the second embodiment.

The position of the anode 21 is dislocated from an original position due to the thermal expansion or the like, so that the focal spot of X-ray beam 24 is deviated from the original path. When this deviation occurs, the irradiation direction of an electron beam 23 emanated from an electron gun 22 is altered so that the focal spot position is kept constant. The CT apparatus comprises: a deflection coil 30, provided in tile vicinity of the passage of the electron beam 23, that generates an electric field or a magnetic field to the passing route of the electron beam 23, power supply 29 for the deflection coil 30, which supplies electric power to the deflection coil 30; a collimator 25 provided to control and limit the passage of the X-ray beam emanated from the anode 21, two X-ray detectors 26a, 26b which are provided in the slice direction in order to detect the irradiated X-ray beam 24; A/D converters 27a, 27b connected to the X-ray detectors 26a, 26b, respectively; and a computer 28 connected to the A/D converters and the power supply 29 for controlling the power level to be supplied to the coil 30 based on the detected results from the detectors 26a, 26b.

Figure 8:
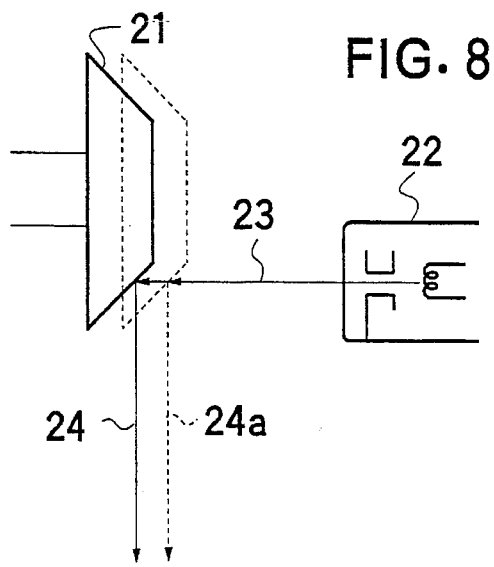
FIG. 8 illustrates a state showing a change of the X-ray beam path (dotted line) when a thermal expansion of the X-ray tube occurs.

Referring to FIG. 8, when the position of the anode 21 is moved to a position 21a due to the thermal expansion, a passing route of the X-ray beam 24 is changed to a passing route 24a. When this occurs, the X-ray amounts detected in the two detectors 26a, 26b (FIG. 7) differ from each other, so that there is caused a difference between ratios of the outputs in the detectors 26aand 26b.

Referring to FIG. 15 in relation to the above description (FIG. 7 , FIG. 8, FIG. 10 and FIG. 11), when the focal spot position is changed due to the thermal expansion of the anode or the like, there occurs a change in the profile (output distribution of the X-ray amount) on the focal spot position detecting units that receive and detect the X-ray beam stopped down at the slit. Thus, the X-ray amounts received at the detectors A, B are different. Then, the outputs may be processed using the following functions, and functions f1 or f2 may be made as a barometer (the output ratio) for the focal spot position in order to monitor the focal spot position of the X-ray tube.

$$f1=(A-B)/(A+B) \text{ or}$$

$$f2=0.5 \text{ in } (A/B)$$

Figure 9:
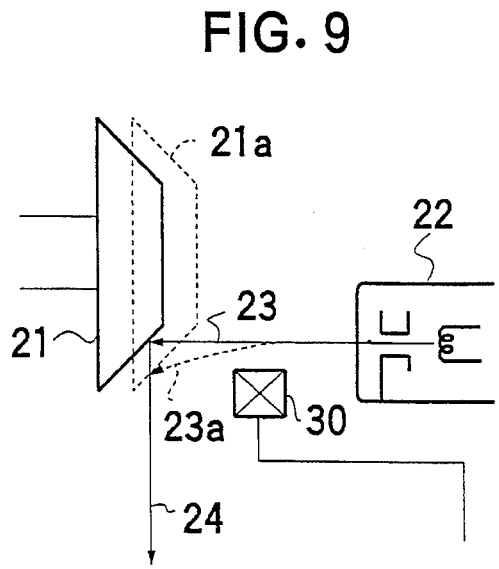
FIG. 9 Illustrates an example in which an electron beam path is deflected by a deflection coil 30, according to the second embodiment.

Then, the computer 28 sends a control signal to a coil supply 29 (the power supply for the deflection coil) based on the change in the output ratios detected by the detectors 26a, 26b. By the signal from the computer 28, the deflection coil 30 provides the electric field or the magnetic field in tile passing route of the electron beam 23, so that the electron beam 23 is deflected as shown in FIG. 9. Referring to FIG. 9, thereby, the path of the electron beam 23 is altered to one indicated as 23a (dotted curve), so that the path of the X-ray beam can be kept the same as in the state prior to the thermal expansion.

Moreover, the magnitude of the electric field or the magnetic field can be stored beforehand in the computer 28 based on empirically collected data on the relation between the output ratios of the X-ray detectors 26a, 26b, and the displaced amount of the anode position. As a result, immediately after the output ratios are detected, the necessary magnitude or the electric field or the magnetic field is determined so as to control the passing route of the electron beam 23.

As described above, according to the second embodiment, when the position of the anode 21 is changed due to the thermal expansion or the like, the focal spot position of the X-ray beam 24 is kept at a constant beam path without really changing the position of the X-ray tube itself.

Though there are provided two X-ray detectors 26a, 26b in the slice direction in FIG. 7, there may be provided a plurality of detectors in the channel direction that is perpendicular to the slice position. Similar alternative is already described in FIG. 11 and FIG. 12 as the one-dimensional case and the two-dimensional case which are depicted above in EXAMPLES OF HOW TO CALCULATE DISLOCATED AMOUNT OF THE FOCAL SPOT POSITION OF THE X-RAY TUBE 6.

In summary, by employing the present invention, the alignment of the focal spot position of the X-ray tube is automatically and optimally performed, at the time that the X-ray tube is replaced anew and the maintenance and inspection is carried out. Thereby, the burden to the service attendant is significantly reduced. Moreover, the alignment of the focal spot position for the X-ray tube can be performed during the scanning operation for clinical use. Thereby, the occurrence of the ring-like image artifact due to the deviation of the focal spot position can be substantially eliminated.

Moreover, when the position of the anode 21 is changed due to the thermal expansion or the like, the focal spot position of the X-ray beam 24 is kept at a constant beam path without really changing tile position of the X-ray tube itself.

Besides those already mentioned above, many modifications and variations of the above embodiments may be made without departing from the novel and advantageous features of tile present invention. Accordingly, all such modifications and variations are intended to be included within the scope of the appended claims.

What is claimed is:

1. An X-ray computerized tomographic (CT) apparatus having an X-ray detector, the apparatus comprising:

an X-ray tube which is freely movable in at least one of a horizontal direction and a vertical direction;

detection means disposed in the vicinity of the X-ray detector for detecting a dislocated degree of the focal spot position of the X-ray tube; and means for automatically controlling the focal spot position of the X-ray tube based on data obtained from the detection means so that the focal spot position of the X-ray tube remains fixed in a predetermined position;

where the detection means includes a storage means for storing a thermal information table of the X-ray tube in advance of a detecting process, so that the dislocated degree of the focal spot position of the X-ray tube is calculated.

2. An X-ray computerized tomographic (CT) apparatus having an X-ray detector, the apparatus comprising:

an X-ray tube which is freely movable in at least one of a horizontal direction and a vertical direction;

detection means, disposed in the vicinity of the X-ray detector, for detecting a dislocated degree of the focal spot position of the X-ray tube; and means for automatically controlling the focal spot position of the X-ray tube based on data obtained from the detection means so that the focal spot position of the X-ray tube remains fixed in a predetermined position;

wherein the focal spot position controlling means includes deflection means for deflecting an electron beam emanated from an electron generating means by an electric field or a magnetic field, so that the focal spot position of the X-ray tube remains fixed in a predetermined position even when the focal spot position is deviated.

3. An X-ray computerized tomographic (CT) apparatus for use with a continuous scanning operation, having an X-ray detector, the apparatus comprising:

an X-ray tube which is freely movable in at least one of a horizontal direction and a vertical direction;

detection means for detecting dislocated degrees of the focal spot position of the X-ray tube at a plurality of rotation positions during a single scanning rotation of a gantry; and averaging means by which the an average value calculated from the plural dislocated degrees detected by the detection means; and means for automatically controlling the focal spot position of the X-ray tube in a next scanning rotation of the gantry, based on data, including the average value for a preceding rotation, obtained from the averaging means.

4. An X-ray computerized tomographic (CT) apparatus for use with a continuous scanning operation, having an X-ray detector, the apparatus comprising:

an X-ray tube which is freely movable in at least one of a horizontal direction and a vertical direction;

detection means, disposed in the vicinity of the X-ray detector, for detecting a dislocated degree of the focal spot position of the X-ray tube; and means for automatically controlling the focal spot position of the X-ray tube based on data obtained from the detection means so that the focal spot position of the X-ray tube remains fixed in a predetermined position, wherein the detection means includes a detection timing means for controlling an instance of detection and aligning the focal spot position by utilizing only an output of the X-ray amount detected at a predetermined position of a gantry.

5. The apparatus of claim 4, wherein the continuous scanning operation includes a helical scanning operation.

6. The apparatus of claim 4, wherein the continuous scanning operation includes a dynamic scanning operation.

7. The apparatus of claim 4, wherein the detection means includes a storage means for storing a thermal information table of the X-ray tube in advance of a detecting process, so that the dislocated degree of the focal spot position of the X-ray tube is calculated.

8. The apparatus of claim 4, wherein the focal spot position controlling means includes drive means for changing at least one of the position of a housing of the X-ray tube, an insert tube of the X-ray tube and a filament of the X-ray tube.

9. The apparatus of claim 4, wherein the detection timing means is controlled such that when a focal spot position control response time is less than a predetermined time, alignment of the focal spot position is made for every projection sequence, while when the focal spot position control response time is greater than the predetermined time, used is only an output of the X-ray amount detected at a predetermined position of a gantry.

10. The apparatus of claim 9, wherein the detection timing means is controlled by taking an average value for a plurality of projections so that the alignment of the focal spot position is made for every time length of the plurality of projections by which the average value is obtained.

11. The apparatus of claim 4, wherein the detection means, disposed in the vicinity of the X-ray detector, includes: an opening portion through which X rays emitted from the X-ray tube pass; and a focal spot position detecting unit having a region divided into at least two portions in order to detect the X-rays passing through the opening portion, and wherein the dislocated degree is detected when there is caused a change in amount of X-rays detected at the least two portions of the focal spot position detecting unit.

12. The apparatus of claim 11, wherein the opening portion in the detection means has a slit opening portion which is disposed vertical to a dislocation direction in order to detect the dislocated degree of the focal spot position in a one-dimensional direction.

* * * * *